United States Patent
Samset et al.

(10) Patent No.: US 9,622,724 B2
(45) Date of Patent: Apr. 18, 2017

(54) ULTRASOUND IMAGING SYSTEM AND METHOD FOR TRACKING A SPECULAR REFLECTOR

(71) Applicant: General Electric Company, Schenectady, NY (US)

(72) Inventors: Eigil Samset, Oppegård (NO); Anders Rasmus Sørnes, Oslo (NO); Raja Sekhar Bandaru, Oslo (NO)

(73) Assignee: General Electric Company, Schenectady, NY (US)

( * ) Notice: Subject to any disclaimer, the term of this patent is extended or adjusted under 35 U.S.C. 154(b) by 235 days.

(21) Appl. No.: 14/230,491

(22) Filed: Mar. 31, 2014

(65) Prior Publication Data

US 2015/0272549 A1    Oct. 1, 2015

(51) Int. Cl.

| | | |
|---|---|---|
| *A61B 8/00* | (2006.01) | |
| *A61B 8/08* | (2006.01) | |
| *G01S 7/52* | (2006.01) | |
| *G01S 15/89* | (2006.01) | |
| *A61B 34/20* | (2016.01) | |

(52) U.S. Cl.
CPC .......... *A61B 8/5207* (2013.01); *A61B 8/0841* (2013.01); *A61B 8/5215* (2013.01); *G01S 7/52036* (2013.01); *G01S 7/52046* (2013.01); *G01S 7/52077* (2013.01); *A61B 8/4488* (2013.01); *A61B 8/463* (2013.01); *A61B 8/483* (2013.01); *A61B 8/5269* (2013.01); *A61B 2034/2063* (2016.02); *G01S 15/8915* (2013.01)

(58) Field of Classification Search
USPC ........................................................ 600/443
See application file for complete search history.

(56) References Cited

U.S. PATENT DOCUMENTS

| | | | | |
|---|---|---|---|---|
| 4,159,462 A | * | 6/1979 | Rocha | G01S 7/52026 367/105 |
| 6,048,312 A | * | 4/2000 | Ishrak | A61B 8/0833 128/916 |
| 2002/0173719 A1 | * | 11/2002 | Zhao | A61B 8/0833 600/437 |
| 2007/0016019 A1 | * | 1/2007 | Salgo | A61B 5/1075 600/437 |
| 2011/0249878 A1 | | 10/2011 | Pagoulatos et al. | |

(Continued)

FOREIGN PATENT DOCUMENTS

| | | |
|---|---|---|
| EP | 2494926 A1 | 9/2012 |
| JP | 2004208859 A | 7/2004 |

OTHER PUBLICATIONS

Kozak et al (Error analysis for determination of accuracy of an ultrasound navigation system for head and neck surgery).*

(Continued)

*Primary Examiner* — Joel F Brutus

(57) ABSTRACT

An ultrasound imaging system and method includes identifying, with a processor, a subset of the ultrasound channel data with a specular reflector signature, and implementing, with the processor, a specular reflector processing technique on the subset of the ultrasound channel data to calculate at least one of a position and an orientation of a specular reflector. The system and method includes performing an action based on at least one of the position and the orientation of the specular reflector.

20 Claims, 8 Drawing Sheets

(56) References Cited

U.S. PATENT DOCUMENTS

2012/0004545 A1* 1/2012 Ziv-Ari .............. G01S 15/8906
  600/437

OTHER PUBLICATIONS

International Search Report and Written Opinion regarding International Application No. PCT/2015/022193, mailed on Jun. 15, 2015, 12 pages.
English language translation of JP2004208859, dated Jun. 2, 2015, 14 pages.

* cited by examiner

ULTRASOUND IMAGING SYSTEM AND METHOD FOR TRACKING A SPECULAR REFLECTOR

FIELD OF THE INVENTION

This disclosure relates generally to an ultrasound imaging system and method for tracking a specular reflector based on ultrasound channel data and performing an action based on at least one of a position and an orientation of the specular reflector.

BACKGROUND OF THE INVENTION

Conventional ultrasound beamforming techniques assume that received acoustic reflections are from diffuse reflectors that reflect ultrasound energy in substantially all direction. This assumption proves useful and effective when imaging soft tissue in a patient. However, the underlying physics for specular reflections is significantly different than for diffuse reflections. A specular reflection is a mirror-like reflection obtained from insonifying a hard level surface with ultrasonic energy. Specular reflections are common when imaging metal objects, including interventional devices and implantable devices. Instead of reflecting ultrasound energy in substantially all directions as is the case with a diffuse reflection, specular reflections are typically very strong at positions where an angle of reflection of the reflected beam is equal to an angle of incidence, and specular reflections generate very little signal at most other locations.

Specular reflectors may contribute to imaging artifacts including a haze artifact in the region close to the specular reflector. If the specular reflector is thin enough, it may also contribute to a ringing artifact that is produced from ultrasound waves that are reflected back-and-forth within the specular reflector. Both the haze artifact and the ringing artifact may degrade any resulting ultrasound images and, in extreme cases, they may even lead to clinicians making inaccurate conclusions based on the ultrasound data.

It is desirable to use ultrasound imaging to track the real-time position of interventional devices such as catheters, guide wires, needles and other devices, which are typically specular reflectors. Conventional ultrasound imaging systems may receive very strong reflected signals from specular reflectors when the specular reflector is perpendicular to a transducer array of the system. In situations where the specular reflector is positioned so that very little or none of the reflected ultrasound energy hits the transducer array, it will not be possible to image the specular reflector. However, according to yet other situations, some of the specularly reflected ultrasound energy may hit the array. This will result in a very intense signal in just a few of the channels corresponding to elements where the angle of incidence equals the angle of reflection. However, in all other channels there will be very little ultrasound signal received from the specular reflector. Standard beamforming techniques assume that that the reflectors behave as diffuse reflectors. As such, standard beamforming techniques typically sum signals from a plurality of channels in order to form an ultrasound image. While this approach has proven very effective for soft tissue and other circumstances where the imaged material behaves like a diffuse reflector, it is ineffective when imaging specular reflectors. The specular reflector will not contribute significant signal to elements other than the elements where the angle of incidence is equal to the angle of reflection. If a conventional beamforming technique is applied to ultrasound data including a specular reflection, the contributions of the specular reflector tend to get minimized during the summing process. Therefore, conventional beamforming techniques are not effective for imaging specular reflectors.

It is often desirable to display the position of an interventional device on an ultrasound imaging system. Conventional systems may use an external tracking system, such as an electromagnetic tracking system or an optical tracking system to determine the location of an interventional device in real-time. However, using an external tracking system adds additional expense and complexity to the entire system. Additionally, the ultrasound system is required to be configured to interface with the tracking system if data showing the location and/or the trajectory of the interventional device is to be displayed in real-time.

It is also known to use a needle guide that acts as a fixture keeping the probe in a constant relative position with respect to a needle being imaged. While this technique is effective for imaging needles, the needle guide combined with the probe and the needle is bulkier and potentially more difficult to maneuver than a stand-alone needle. Additionally, this technique does not work to track other types of interventional devices that are disposed completely within the patient.

For these and other reasons an improved method and ultrasound imaging system for tracking specular reflectors and performing an action based on the position and/or the orientation of the specular reflector is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging with an ultrasound imaging system including a processor and a display device includes acquiring ultrasound channel data, and identifying, with the processor, a subset of the ultrasound channel data with a specular reflector signature. The method includes implementing, with the processor, a specular reflector processing technique on the subset of the ultrasound channel data to calculate at least one of a position and an orientation of a specular reflector. The method includes performing an action, with the processor, based on at least one of the position and the orientation of the specular reflector.

In an embodiment, an ultrasound imaging system includes a probe, a display device, a receiver in electronic communication with the probe, and a processor in electronic communication with the receiver and the display device. The processor is configured to receive ultrasound channel data from the receiver and identify a subset of the ultrasound channel data with a specular reflector signature. The processor is configured to implement a specular reflector processing technique on the subset of the ultrasound channel data to calculate at least one of a position and an orientation of a specular reflector. The processor is configured to perform an action based on at least one of the position and the orientation of the specular reflector.

In another embodiment, a method of ultrasound imaging within a patient with an ultrasound imaging system including a processor and a display device includes manipulating an interventional device within a region of interest in the patient. The method includes acquiring ultrasound channel data of the region of interest and performing the following steps in real-time as the interventional device is manipulated. Identifying, with the processor, a subset of the ultrasound channel data with a specular reflector signature. Implementing, with the processor, a specular reflector processing technique on the subset of the ultrasound channel data to calculate at least one of a position and an orientation of the interventional device. Beamforming the ultrasound channel data according to a summing technique to generate an ultrasound image. Generating, with the processor, an enhanced representation of the specular reflector, and displaying the enhanced image on the ultrasound image to show the position of the interventional device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
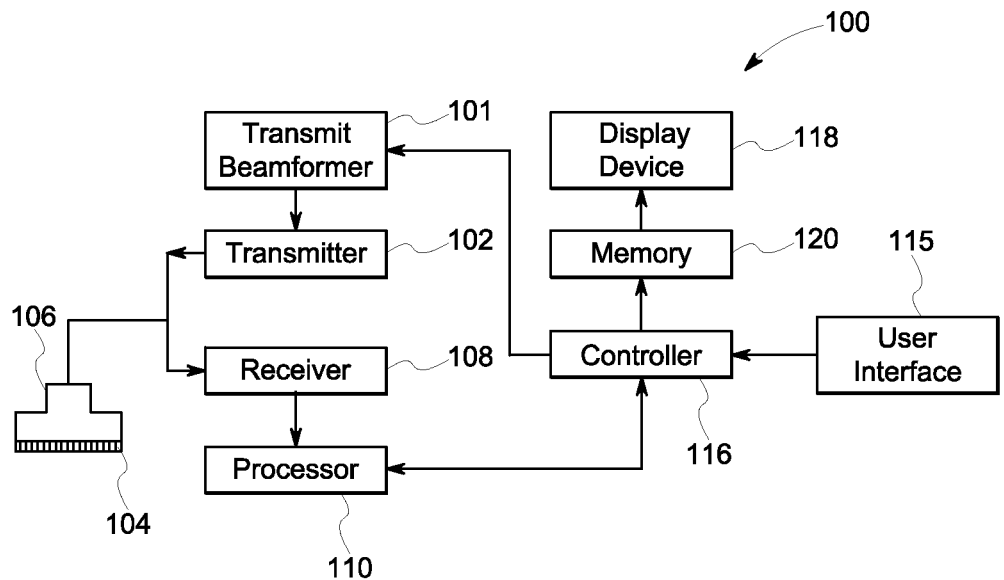
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a tissue (not shown). The probe 106 may be a linear array, a phased array, a curved array, a mechanical 3D probe, or a 2D matrix array probe, or any other type of ultrasound probe according to various embodiments. According to exemplary an exemplary embodiment, the probe 106 may be a 2D matrix array probe to allow for full steering in both the azimuth and elevation directions. The pulsed ultrasonic signals are backscattered from structures in the tissue, like blood cells or muscular tissue, to produce echoes that return to the elements 104. The echoes are converted into electrical signals, or ultrasound channel data, by the elements 104, and the electrical signals are received by a receiver 108. For purposes of this disclosure, the term "ultrasound channel data" will be defined to include data from a plurality of different channels prior to beamforming. Ultrasound channel data may therefore refer to data from either the probe 106 or the receiver 108. The processor 110 receives the ultrasound channel data from the receiver 108. The processor 110 may comprise one or more processors including any one or more of the following: a graphics processing unit (GPU), a microprocessor, a central processing unit (CPU), a digital signal processor (DSP), or any other type of processor capable of performing logical operations. The processor 110 may comprise a software beamformer, but it should be appreciated that the processor 110 may be separate from the software beamformer in other embodiments. As stated above, the processor 110 receives ultrasound channel data from the receiver 108. The processor 110 then applies the appropriate delays to the ultrasound channel data in order to focus on specific locations within a region or volume of interest. The processor 110 may be configured to perform retrospective transmit beamforming on the ultrasound channel data.

The processor 110 may be adapted to perform one or more processing operations according to a plurality of selectable ultrasound modalities on the ultrasound channel data. The ultrasound channel data may be processed in real-time during a scanning session as the echo signals are received. For the purposes of this disclosure, the term "real-time" is defined to include a procedure that is performed without any intentional delay. For example, an embodiment may acquire and display data a real-time frame-rate of 7-20 frames/sec. However, it should be understood that the real-time frame rate may be dependent on the length of time that it takes to acquire each frame of data. Accordingly, when acquiring a relatively large region or volume of data, the real-time frame-rate may be slower. Thus, some embodiments may have real-time frame-rates that are considerably faster than 20 frames/sec, while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown), and/or multi-core processors to handle the processing tasks.

According to other embodiments (not shown), the processor 110 shown in FIG. 1 may be replaced with two or more separate components. For example, an embodiment may include a processor and a separate software beamformer (not shown) that are both in parallel between the receiver 108 and a controller 116. According to this embodiment, both the processor and the software beamformer would receive ultrasound channel data from the receiver 108. The software beamformer would, for example, perform beamforming operations and the processor would perform calculations related to the identification of specular reflectors in the ultrasound channel data. According to an embodiment, the processor may calculate the position and orientation of the specular reflectors in the data and transmit coordinates specifying the positions and/or orientations of any specular reflectors to the controller 116. According to another embodiment, the software beamformer may generate an image based on the ultrasound channel data and the processor may produce a secondary image. The secondary image may, for instance, include information showing a representation of a specular reflector. The controller 116 may display the secondary image as an overlay on top of the standard ultrasound image, or the secondary image may replace either some or all of the standard ultrasound image. Various ways of displaying information related to any specular reflectors will be described hereinafter according to various embodiments.

According to some exemplary embodiments, the probe 106 may contain the components to do some or all of the transmit and/or the receive beamforming. For example, all or part of the transmit beamformer 101, the transmitter 102, the receiver 108 and the processor 110 may be situated within the probe 106. The terms "scan" or "scanning" may also be used in this disclosure to refer to acquiring data through the process of transmitting and receiving ultrasonic signals. Additionally, the terms "data" or "ultrasound channel data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes the controller 116 to control the transmit beamformer 101, the transmitter 102, and the receiver 108. The controller 116 may control the processor 110 according to some embodiments. According to other embodiments, the processor 110 may be a sub-component of the controller 116. According to other embodiments, the processor 110 may output images for display directly to the memory 120 or to the display device 118, instead of transmitting processed data to the controller 116 as shown in FIG. 1. Referring back to FIG. 1, the controller 116 is in electronic communication with the probe 106. The controller 116 may control the probe 106 to acquire data. The controller 116 controls which of the elements 104 are active and the shape of a beam emitted from the probe 106. The controller 116 is also in electronic communication with a display device 118, and the controller 116 may process the ultrasound channel data into images for display on the display device 118. For purposes of this disclosure, the term "electronic communication" may be defined to include both wired and wireless connections. The controller 116 may include a central processor (CPU) according to an embodiment. According to other embodiments, the controller 116 may include other electronic components capable of carrying out processing functions, such as a digital signal processor, a field-programmable gate array (FPGA) or a graphic board. According to other embodiments, the controller 116 may include multiple electronic components capable of carrying out processing functions.

The ultrasound imaging system 100 may continuously acquire ultrasound channel data at a frame-rate of, for example, 10 Hz to 30 Hz. Images generated from the ultrasound channel data may be refreshed at a similar frame-rate. Other embodiments may acquire and display ultrasound channel data at different rates. For example, some embodiments may acquire ultrasound channel data at a frame-rate of less than 10 Hz or greater than 30 Hz depending on the size of the region of interest and the intended application. A memory 120 is included for storing processed image frames for display at a subsequent time. Each image frame may include an associated time stamp indicating the time or relative time of acquisition to facilitate retrieval in the proper sequence from the memory 120. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring ultrasound channel data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, ultrasound channel data may be processed by other or different mode-related modules by the processor 110 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
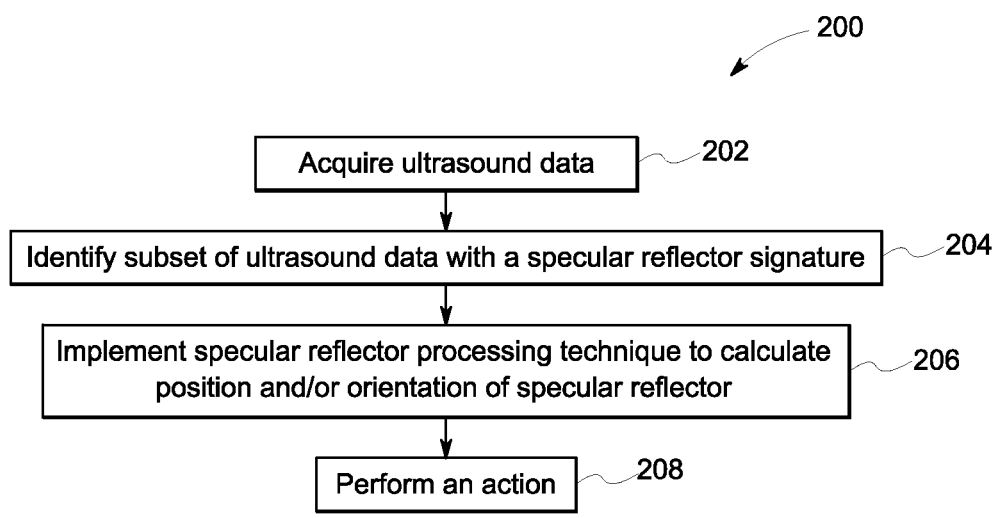
FIG. 2 is a flow chart of a method in accordance with an embodiment.

FIG. 2 is a flow chart of a method in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the performance of an action based on at least one of a position and an orientation of a specular reflector.

Referring now to FIGS. 1 and 2, at step 202, the controller 116 controls the transmit beamformer 101, the transmitter 102, and the probe 106 to acquire ultrasound channel data. The ultrasound channel data may comprise 2D ultrasound channel data or 3D ultrasound channel data. Each channel may carry the data from one or more elements 104 in the probe 106. The ultrasound channel data may be acquired along a plurality of lines in a direction substantially perpendicular to the face of the probe 106 or some or all of the lines may be steered in either an azimuth or an elevation direction so that the lines are not perpendicular to the face of the probe 106. According to another embodiment, unfocused ultrasound energy may be used to acquire ultrasound channel data during step 202. For example, plane waves, spherical waves, or any other type of unfocused transmission schemes may be used to acquire the ultrasound channel data during step 202 in additional to various types of focused transmit beams. The controller 116 may, for instance, control the transmit beamformer 101 and the transmitter 102 to emit a transmit beam with a discrete focal point within the region or volume of interest. Next, the probe 106 receives reflected ultrasound signals along each line. The receiver 108 receives unprocessed or raw ultrasound channel data from all of the elements 104 that are in the active receive aperture of the transducer array. The processor 110 may process the raw ultrasound channel data in order to form pixel or voxel values at a plurality of different points representing different depths along each scan line. The processor 110 has access to the raw ultrasound channel data representing data from each channel. After receiving the raw ultrasound channel data, the software beamformer may apply the appropriate delays to the ultrasound channel data in order to focus at specific depths along each scan line. The processor 110 may also emulate a conventional hardware beamformer and dynamically focus the receive beam as a function of depth along each scan line. The software beamformer may be configured to perform multi-line acquisition (MLA). For example, the processor 110 may acquire 2, 4, 6, 8, or 16 receive lines for each transmit line. It should be appreciated that the processor 110 may acquire a different number of receive lines for each transmit line according to other embodiments.

According to another acquisition scheme, the controller 116 may control the transmit beamformer 101 and the transmitter 102 to transmit two or more different waves with different foci, so that each location within a field-of-view is insonified from at least two different directions. Therefore, at least two samples are acquired from multiple directions for each location in the field-of-view. The processor 110 may receive the ultrasound channel data from the probe 106 and apply retrospective dynamic focusing (RTF) to the ultrasound channel data. When performing RTF, the processor 110 applies a time offset to at least one of the two or more samples acquired at each location. The processor 110 may then combine the samples after the offset has been applied. Applying the offset allows for the samples to be combined in-phase and the processor 110 can thus generate an image using the samples acquire based on two or more different transmit events, each with a different focus. According to another embodiment, the controller 116 may control the transmit beamformer 101 to emit unfocused ultrasound energy such as, for example, plane waves or spherical waves.

Referring to FIG. 2, at step 204, the processor 110 identifies a subset of the ultrasound channel data with a specular reflector signature. Techniques used to identify the subset of the ultrasound channel data will be described in detail hereinafter.

Figure 3:
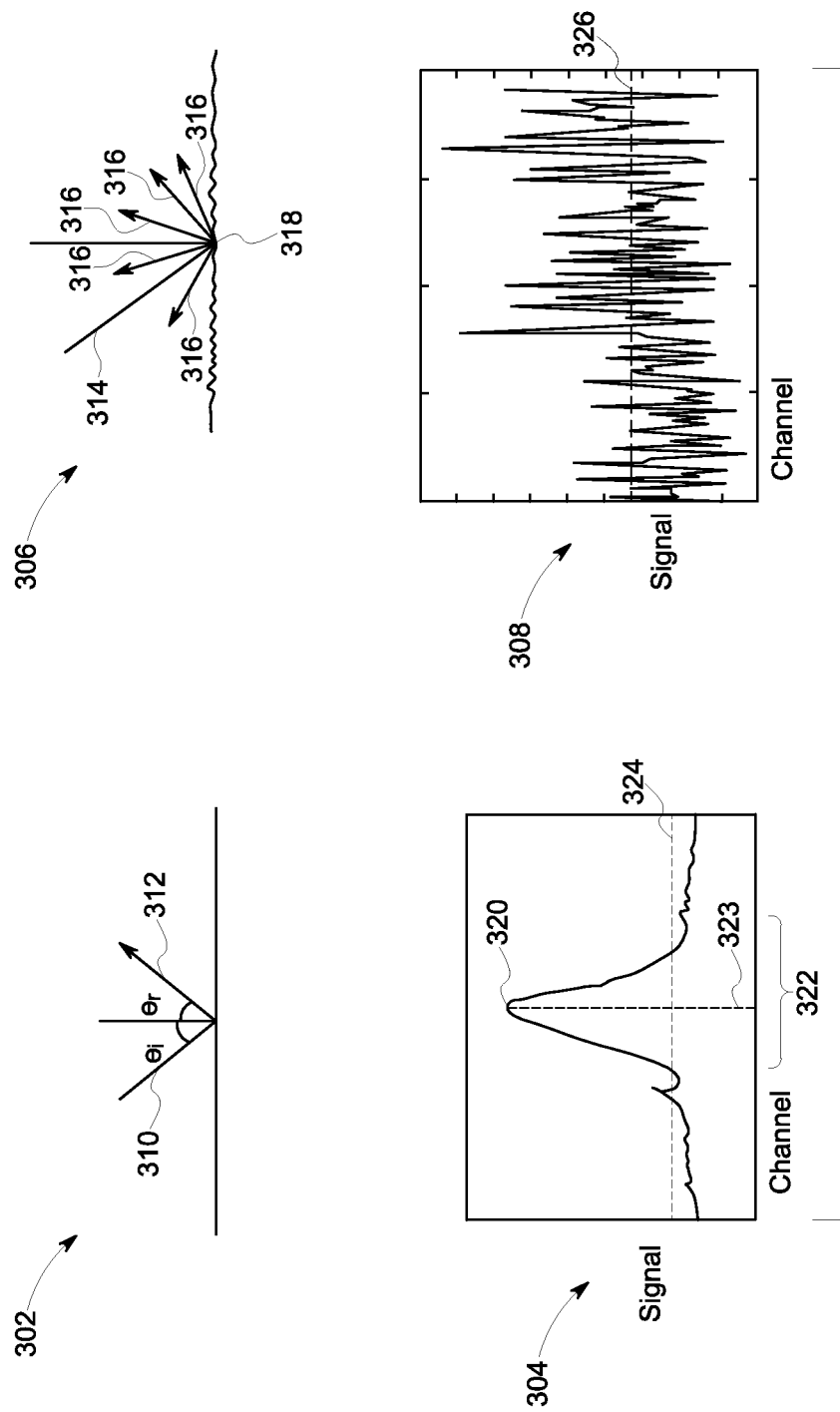
FIG. 3 is a schematic representation of a specular reflection and a diffuse reflection in accordance with an embodiment.

FIG. 3 is a schematic representation of a specular reflection 302 and a non-specular or diffuse reflection 306. FIG. 3 includes a graphical representation of the specular reflection 302, a specular beam profile 304, a graphical representation of the diffuse reflection 306, and a diffuse beam profile 308. The graphical representation of the specular reflection 302 includes an incident beam 310 and a reflected beam 312. The reflected beam 312 has an angle of reflection $\theta_r$ that is equal to an angle of incidence $\theta_i$. The diffuse reflection includes an incident beam 314 and a plurality of reflected beams 316. Each of the plurality of reflected beams 316 is reflected in a different direction originating from a point 318. It should be noted that the surface shown in the diffuse reflection 306 is shown as bumpy and irregular, whereas the surface shown in the specular reflection 302 is shown as smooth. Specular reflections are typically more prevalent with when the surface is smooth, as shown in the specular reflection 302.

The specular beam profile 304 shows a distinct peak 320 with relatively high amplitude. The amplitude of the peak 320 may be on generally the same order as the transmit pulse according to some embodiments. Most of the received signal is within a set distance of a location 323 of the peak. In contrast, the diffuse beam profile 308 does not have a distinct peak. Instead, the diffuse beam profile 308 is jagged and has multiple peaks spread out over a plurality of different channels. The diffuse beam profile 308 includes multiple local maxima due to the fact that each diffuse reflection generates a plurality of reflected beams as shown in the diffuse reflection 306.

Figure 4:
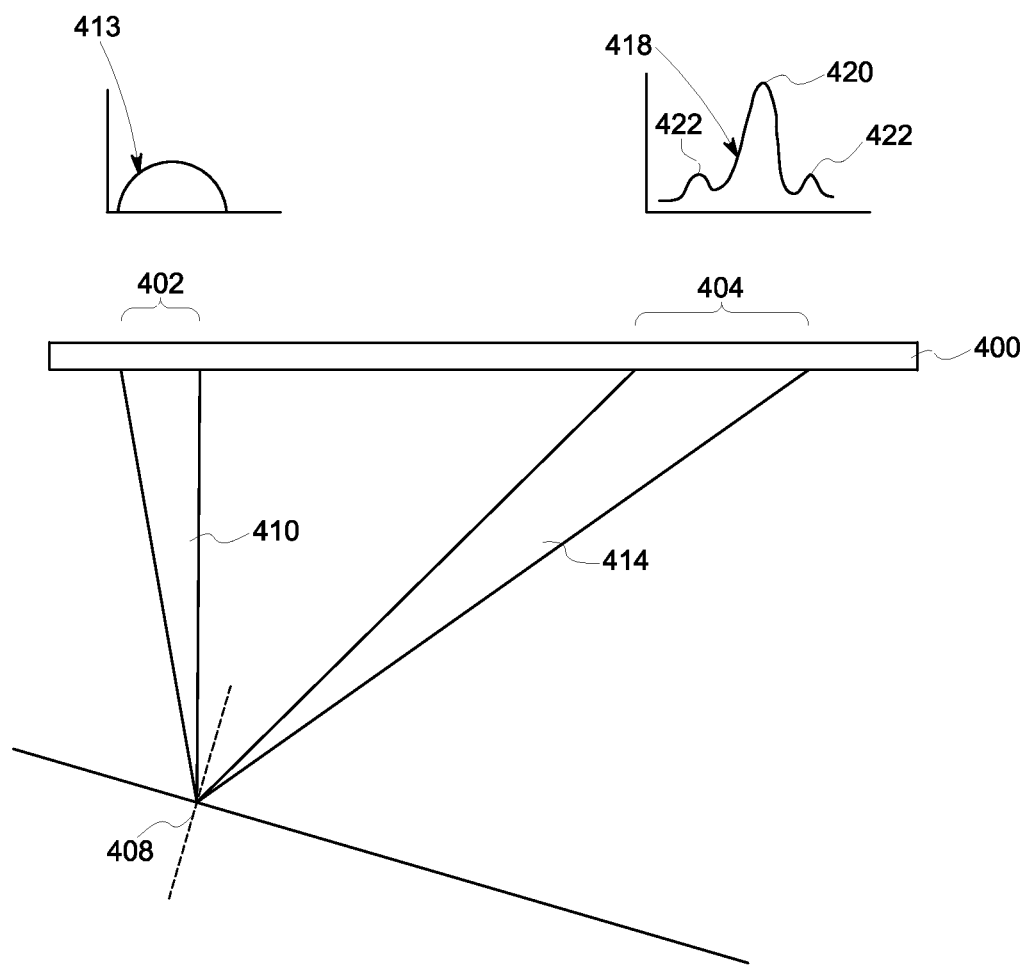
FIG. 4 is a schematic representation of a specular reflection in accordance with an embodiment.

FIG. 4 is a schematic representation of a specular reflection in accordance with an embodiment. FIG. 4 includes a transducer array 400 including a plurality of element (not shown). The transducer array 400 includes a transmit aperture 402 comprising a first plurality of transducer elements and a receive aperture 404 comprising a second plurality of transducer elements. The first plurality of elements in the transmit aperture 402 are controlled to emit a transmit beam 410. The transmit beamformer 101 and the transmitter 102 apply delays to the first plurality of elements in the transmit aperture 402 to focus the transmit beam 410 at point 408, which is shown on surface of a specular reflector 406. An exemplary transmit beam profile 413 is shown above the elements in the transmit aperture 402. The receive aperture 404 receives reflected beam 414. While the transmit beam profile 413 is generally a convex curve according to an exemplary embodiment, the receive beam profile 418 has a distinct peak 420 that is narrower than the transmit beam profile 413. Additionally, the receive beam profile 418 shown in FIG. 4 includes two local maxima 422.

Referring back to FIG. 2, at step 204, the processor 110 identifies a subset of the ultrasound channel data with a specular reflector signature. As discussed with respect to FIGS. 3 and 4, diffuse reflectors tend to produce diffuse reflections, such as the diffuse reflection 300. Each point of a diffuse reflector that is insonified with ultrasound energy acts to some extent as an unfocused emitter of ultrasound energy. Diffuse reflectors tend to reflect ultrasound energy more-or-less evenly in all directions as shown by the plurality of reflected beams 316. The diffuse beam profile 308 reflects the omnidirectional nature of diffuse reflections since the average signal strength across all the channels in the receive aperture is generally the same, and the peaks shown in the diffuse beam profile 308 are all approximately the same height. Additionally, the peaks in the diffuse beam profile 308 are distributed more-or-less evenly across the channels in the receive aperture.

As described previously, the specular reflection 302 results in a specular profile 304 with the distinct peak 320. When receiving echoes from a specular reflector, the receive channels will show a receive beam profile similar to the specular beam profile 304 in a subset of the channels. The signals in the other receive channels will typically be very low when imaging a specular reflector. Therefore, at step 204 the processor 110 may analyze the channel data for a specular reflector signature. The specular reflector signature may be identified in the channel data by analyzing a distribution or a variance of the received signals in the channel data. For example, an exemplary specular reflector signature for a single point may include relatively low signal values for most of the channels and a single peak such as the peak 320 shown in the FIG. 3. The channels showing the peak indicative of a specular reflector would typically correspond to elements that are located spatially close to each other in the transducer array. The specular beam profile 304, for example, includes the peak 320 from a small number of elements that are adjacent to each other in the transducer array. Another way to identify a subset of the ultrasound channel data with a specular reflector signature is to analyze a variance of the ultrasound channel data. Variance is a measurement of how far the signal value in each channel is from an average signal value. Variance is described by the following equation:

$$\sigma^2 = \frac{\sum (X - \mu)^2}{N}$$

Where $\sigma^2$ is variance, $\mu$ is the mean value across all the channels, N is the number of terms, or channels, in the distribution, and X is the value of the term or signal value of the channel. According to an embodiment, the mean value and the number of channels may both be calculated for each location from which the ultrasound channel data is acquired.

Referring again to FIG. 3, the specular beam profile 304 contains a much higher variance than the diffuse beam profile 308. A mean line 324 represents a mean signal value for the specular profile 304 while a mean line 326 represents a mean signal value for the diffuse profile 308. The specular beam profile 304 contains a relatively high variance compared to the diffuse beam profile 308. According to an embodiment, the processor 110 may determine an average variance based on all of the ultrasound channel data and then use this average variance to identify the subset of the ultrasound channel data with a variance higher than the average variance. The processor 110 may additionally or alternatively use a different technique to identify a threshold for determining whether or not a particular subset of ultrasound channel data represents a specular reflector. For example, the thresholds may be determined based on empirical data or according to any other technique. Additionally, other embodiments may use additional analysis techniques to identify the subset of ultrasound channel data with a specular reflector signature. For example, other algorithms may take into account relative spacing and peak widths of local maxima to see if the local maxima match established criteria for the shape and width of specular profiles. It should be appreciated by those skilled in the art that the processor 110 may implement other techniques on the ultrasound channel data to identify the specular reflector signature. For example, the processor 110 may use other metrics in order to characterize amplitude distribution across the channels including analyzing higher order moments, calculating polynomial fit parameters, or any other statistical technique of identifying a specular reflector signature in ultrasound channel data.

At step 204, the processor 110 may identify a subset of the ultrasound channel data with a specular reflector signature based on 2D ultrasound channel data, 3D ultrasound channel data, or 4D (real-time 3D) ultrasound channel data. While FIGS. 3 and 4 are directed towards embodiments using 2D ultrasound channel data, it should be appreciated by those skilled in the art that processor 110 may analyze 3D or 4D ultrasound channel data in order to identify one or more specular reflector signatures in the data. For example, the processor 110 may analyze the channel data in multiple dimensions to identify one or more specular reflector signatures based on the channel data.

Referring back to FIG. 2, at step 206 the processor 110 implements a specular reflector processing technique to calculate a position and/or an orientation of the specular reflector. As previously described with respect to FIG. 3, the angle of reflection $\theta_r$ that is equal to the angle of incidence $\theta_i$ with respect to the specular reflector 302. The processor 110 may determine a position of the specular reflector based on the subset of ultrasound channel data identified in step 204. In an exemplary processing technique, the processor 110 identifies a location 323 of the peak of the specular beam profile 304. The location 323 corresponds to the channel, which in turn corresponds to the element that received the peak value of the reflected beam. According to other embodiments, the processor 110 may determine a center location of the received beam according to another technique. For example, the processor 110 may implement an averaging function to all the signal values in a central region 322 corresponding to the peak 320 in the distribution.

After identifying the element or location on the transducer array representing the center of the specular reflection, the processor 110 may calculate the position of the specular reflector based on the position from which the transmit beam was emitted and the total time-of-flight of the beam using known ultrasound processing techniques and well-established information about the speed of sound in various tissue. The above-described technique will identify the location of a single point on the surface of the specular reflector. Depending upon the angle of the transmission and the orientation of the specular reflector with respect to the array, it may be possible to calculate the positions of a plurality of points along the surface of the specular reflector. Once the positions of multiple points have been identified, the processor 110 may use the positions of these points to calculate the position and/or the orientation of the reflective surface of the specular reflector. In diagnostic imaging, many times it is useful to track specular reflectors such as catheters, guide wires, or needles. Most of these interventional devices are largely one-dimensional. The processor 110 may determine one or both of the position and the orientation of any of these devices based on the calculated position and/or orientation of the reflective surface.

At step 208 of the method 200, the processor 110 performs an action based on at least one of the position and the orientation calculated at step 206. The step of performing the action may include many different actions according to various embodiments that will be described hereinafter.

Figure 5:
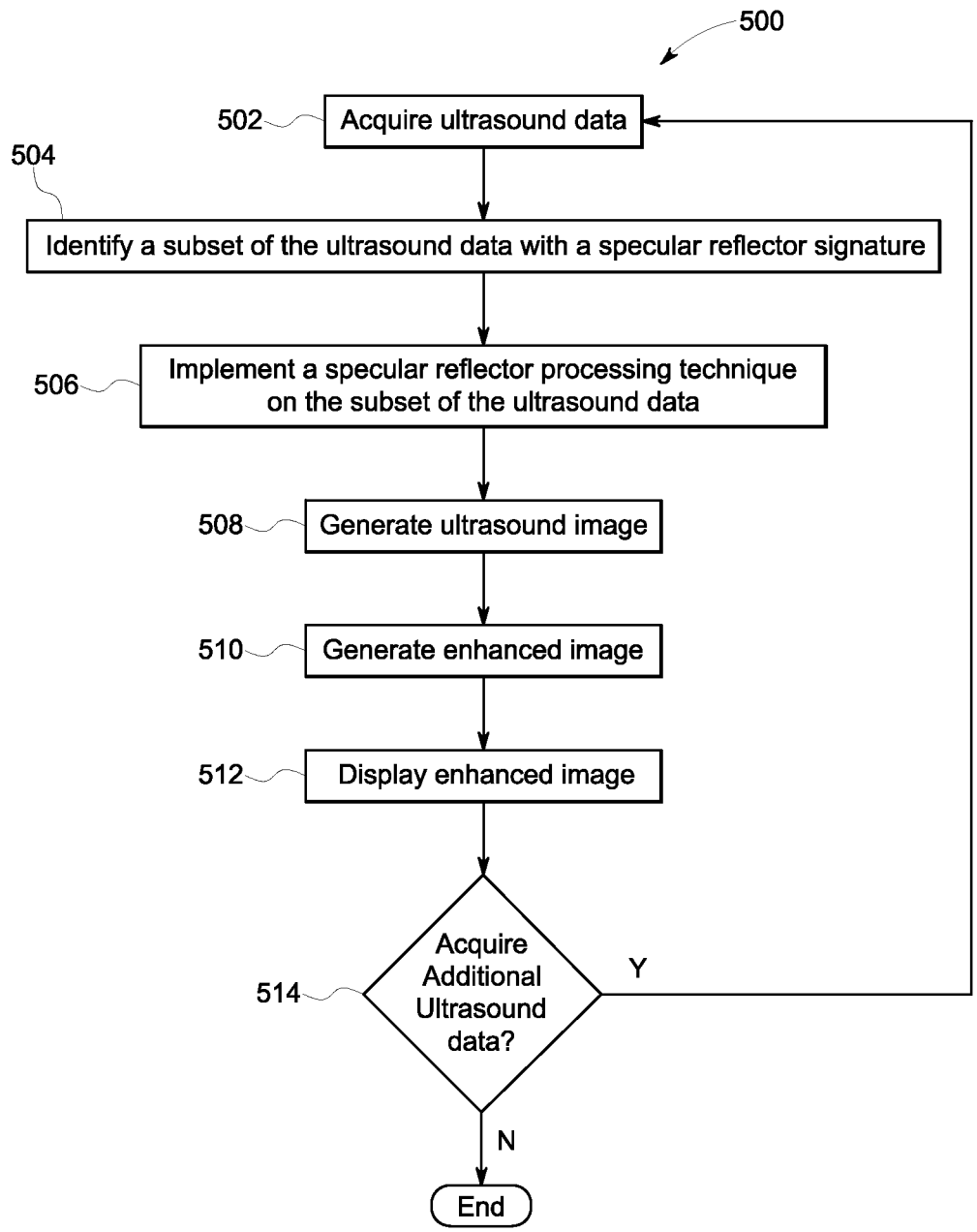
FIG. 5 is a flow chart of a method in accordance with an embodiment.

According to an embodiment, the action may comprise the generation and display of an enhanced image. FIG. 5 is a flow chart of a method in accordance with an exemplary embodiment where the action comprises generating and displaying an enhanced image. The individual blocks of the flow chart represent steps that may be performed in accordance with the method 500. Additional embodiments may perform the steps shown in a different sequence and/or additional embodiments may include additional steps not shown in FIG. 5. The technical effect of the method 500 is the display of an enhanced image.

At step 502 the controller 116 controls the acquisition of ultrasound channel data. At step 504 the processor 110 identifies a subset of ultrasound channel data with a specular reflector signature. At step 506, the processor 110 implements a specular reflector processing technique to identify a subset of the ultrasound channel data with a specular reflector signature. Step 502 is similar to step 202, step 504 is similar to step 204, and step 506 is similar to step 206 that were previously described with respect to the method 200 in FIG. 2. Steps 502, 504, and 506 will therefore not be described in additional detail.

At step 508 the processor 110 generates an ultrasound image based on the ultrasound channel data acquired during step 502. The image may be based on any type of imaging mode. According to an exemplary embodiment, the image may be a B-mode image. At step 510, the processor 110 generates an enhanced image based on the position and/or the orientation of the specular reflector calculated during step 506. Examples and specific details of enhanced images according to various embodiments will be described hereinafter. The processor 110 displays the enhanced image on the display device 118 during step 512.

At step 514 the controller 116 determines if it is desired to acquire additional ultrasound channel data. During real-time ultrasound acquisition and display, the default at step 514 may be to acquire additional ultrasound channel data until a user stops actively scanning a field-of-view. According to other embodiments, the controller 116 may acquire additional ultrasound channel data at a preset or a user-determined interval. If it is desired to acquire additional ultrasound channel data, the steps of 502, 504, 508, 510, 512, and 514 are iteratively repeated. If it is not desired to acquire additional ultrasound channel data, the method 500 may end according to an embodiment.

Figure 6:
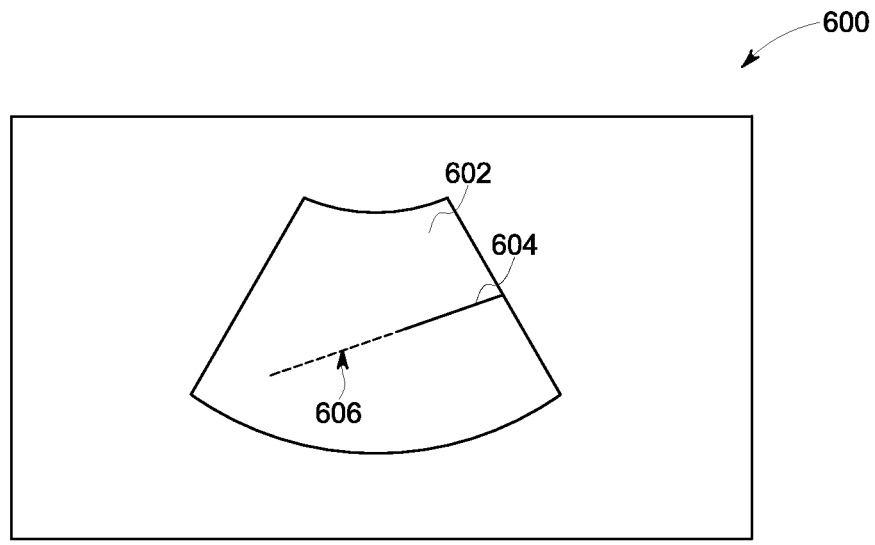
FIG. 6 is a schematic representation of an enhanced image in accordance with an embodiment.

FIGS. 6, 7, 8, and 9 are all examples of enhanced images that may be generated according to the method 500 according to various embodiments. FIG. 6 is a schematic representation of an enhanced image 600 in accordance with an embodiment. Enhanced image 600 includes an ultrasound image 602, a line 604, and an aim line 606. As described with respect to step 508, the ultrasound image may be a B-mode image.

The enhanced representation of the specular reflector may include any way of highlighting or indicating the position and/or orientation of the specular reflector. The enhanced representation of the specular reflector may include may include one or more techniques from the following options: representing the position and/or orientation of the specular reflector with a line or a curve on the enhanced image 600, colorizing the representation of the specular reflector 604 in a color to distinguish the representation of the specular reflector 604 from the ultrasound image 602, displaying an icon to indicate the position and orientation of the specular reflector, and displaying a specular image. The enhanced representation of the specular reflector may be co-displayed at the same time as an ultrasound image generated from the ultrasound channel data according to a conventional ultrasound imaging mode.

The enhanced representation of the specular reflector 604 shown in FIG. 6 comprises line 604 that may be colorized to further differentiate it from the ultrasound image 602. According to an embodiment, the specular reflector may be a needle and the enhanced image 600 may additionally include an aim line 606 to indicate the tissue that the needle would contact if it were inserted deeper into the tissue being imaged along a current trajectory. The aim line 606 is shown as a straight line in FIG. 6, but other embodiments may include a curved aim line in association with interventional devices that would follow a curved trajectory. The user may toggle the aim line 606 between an "OFF" state and an "ON" state. Other embodiments may not include the aim line 606 in the enhanced image.

In another embodiment, an enhanced image may be used to provide the user with an estimate of the distance remaining before a catheter tip would contact muscle or other target tissue. For example, the enhanced image may include an enhanced representation of the catheter including a clearly defined catheter tip. This enhanced image provides the user with a better visualization of the catheter inside the patient's anatomy. An enhanced representation of a catheter may be used, for instance, to help guide real-time EP ablation procedures for treating atrial fibrillation or other cardiac irregularities. The enhanced image may optionally include a scale or a value for an estimated distance remaining between the catheter tip and the target muscle tissue. This estimated distance may be updated in real-time as the position of the catheter is adjusted before and during the EP ablation procedure. It should be appreciated that the catheter tip visualization may be used with procedures other than EP ablation according to other embodiments.

Figure 7:
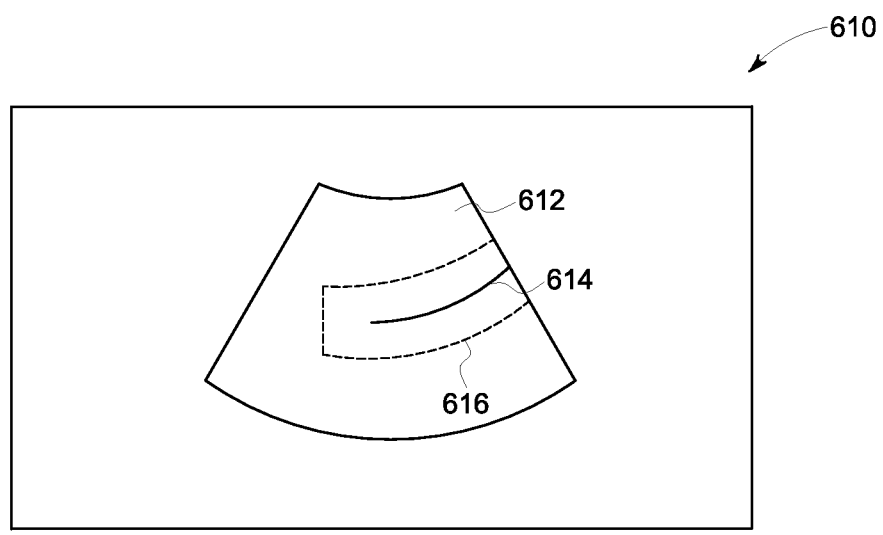
FIG. 7 is a schematic representation of an enhanced image in accordance with an embodiment.

FIG. 7 is a schematic representation of an enhanced image 610 in accordance with an embodiment. The enhanced image 610 includes an ultrasound image 612 and a curve 614. The curve 614 may represent the position and orientation of a curved specular reflector, such as an interventional device. The enhanced representation of the specular reflector 614 may be colorized in order to more clearly differentiate it from the ultrasound image 612. According to another embodiment, the enhanced representation of the specular reflector 614 may be rendered with a higher reflectivity than the non-specular portions of the image. Referring to both FIGS. 2 and 7, according to an embodiment, performing an action at step 208 may comprise removing or reducing a haze artifact from an image. The haze artifact is typically present in an area or volume adjacent to the specular reflector. The processor 110 may, for instance, apply an image processing technique that specifically removes or reduces the haze artifact in a predetermined region close to the specular reflector. FIG. 7 includes a specular reflector 614 and a region 616 a predetermined distance from the specular reflector. The processor 110 may calculate the position of the region 616 after determining the location of the specular reflector 614. Then, the processor 110 may implement the algorithm to reduce or remove the haze artifact specifically in the region 616. When dealing with 3D ultrasound channel data, the processor 110 may identify a volume within a predetermined distance from the specular reflector 614. According to another embodiment, the processor 110 may use the position of the specular reflector as a seed location when implementing the algorithm configured to reduce the haze artifact. By specifically targeting a region or volume near to the specular reflector for the haze reduction algorithm, it is possible to utilize a more aggressive image processing technique to reduce the effects of the haze compared to an algorithm that could be applied to the whole image. This results in a final image with reduced artifacts and improved diagnostic utility.

Figure 8:
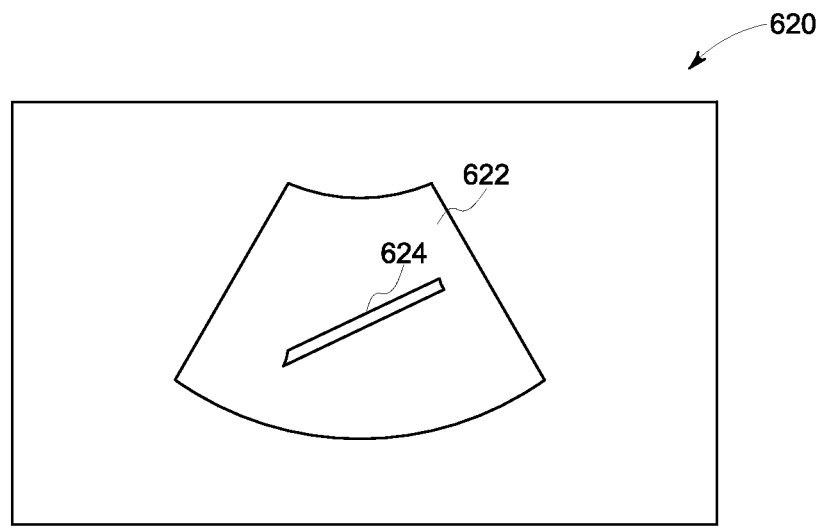
FIG. 8 is a schematic representation of an enhanced image in accordance with an embodiment.

FIG. 8 is a schematic representation of an enhanced image 620 in accordance with an embodiment. The enhanced image 620 includes an ultrasound image 622 and an icon 624 representing the position of the specular reflector with respect to the ultrasound image. According to an embodiment where the specular reflector is an interventional device, the icon 624 may include, for example, a model or a representation of the interventional device. Depending on the position of the specular reflector and the array, it may not be possible to acquire all of the points along the surface of the specular reflector. However, the processor 110 may be able to use the position and/or orientation data calculated at step 506 in order to orient the icon 624 at a position on the ultrasound image 622 indicative of the position and orientation of the interventional device within the tissue being imaged. According to an embodiment, the icon 624 may be selected from a look-up table or from some other type of memory. For example, the icon may be generated from a CAD file with detailed shape and features of the specific interventional device. The user may be able to select the interventional device from a list of interventional devices, or the processor 110 may automatically select the most appropriate icon from the look-up table based on the detected characteristics of the interventional device based on the position and orientation data calculated at step 506. According to an embodiment, the processor 110 may be able to render the icon 624 according to known rendering techniques so that the perspective of the icon 624 correlates with the orientation of the interventional device in the tissue.

Figure 9:
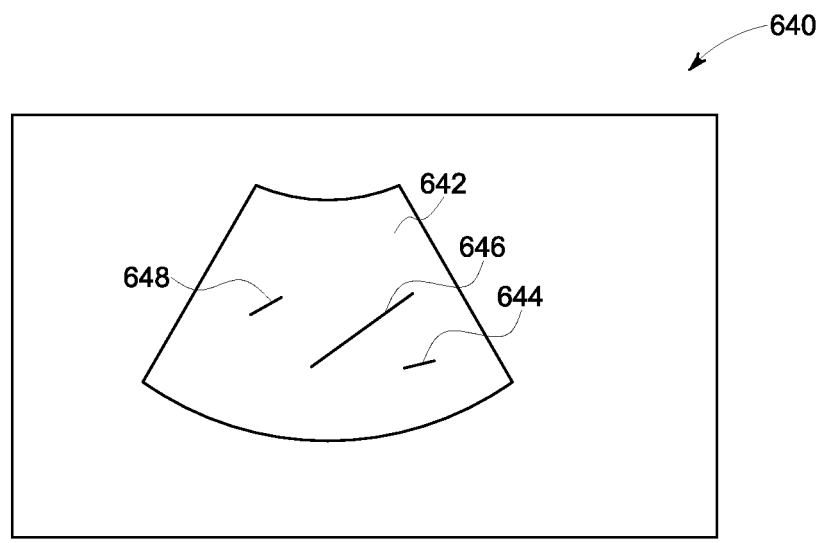
FIG. 9 is a schematic representation of an enhanced image in accordance with an embodiment.

FIG. 9 is a schematic representation of an enhanced image 640 in accordance with an embodiment. The enhanced image 640 includes an ultrasound image 642 and a specular image superimposed on the ultrasound image 642. The specular image may include generating an image based on the position and orientation data of the specular reflector or specular reflectors calculated during step 506. According to another embodiment, the specular image may include an image based on the likelihood of each pixel representing a specular reflector. The probability may be represented by intensity, color, opacity, or any other pixel display parameter. For example, if a pixel is very likely to represent a specular reflector, it may receive a high intensity value. If a pixel is unlikely to represent a specular reflector, it may receive a low intensity value. Additionally, the intensity and/or color of the pixel may be given an intermediate value if there is less certainty about whether or not the pixel represents a specular reflector or a diffuse reflector.

In the enhanced image 640, the specular image includes three discrete shapes that are likely to be specular reflectors. A first line 644, a second line 646, and a line 648. The specular image is comprised of the first line 644, the second line 646, and the third line 648. As discussed above, the specular image may also include indications of areas or regions that are somewhat likely, or somewhat unlikely to represent a specular reflector in other embodiments. An alternative way to think of the specular image is to consider it an image based on the probability of each pixel representing a specular reflector.

Figure 10:
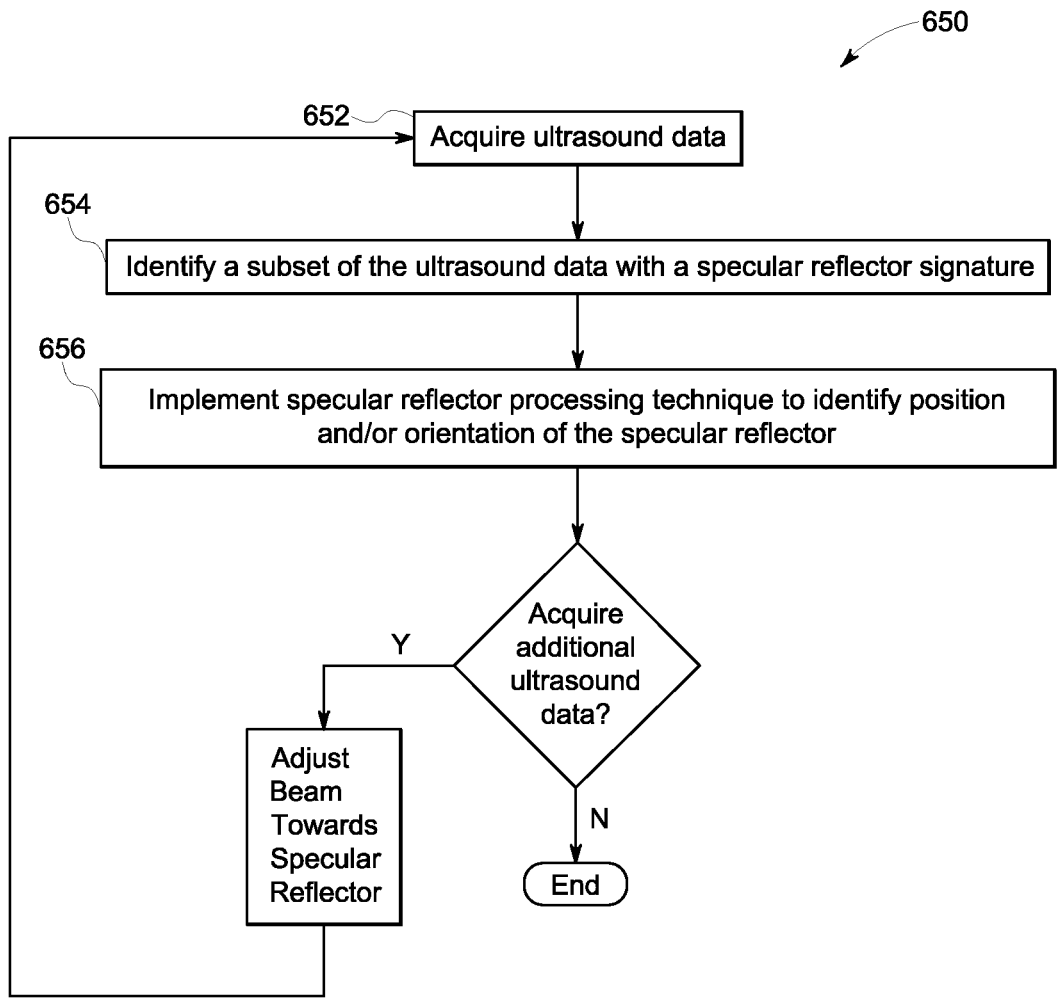
FIG. 10 is a flow chart of a method in accordance with an embodiment.

FIG. 10 is a flow chart of a method 650 in accordance with an exemplary embodiment where performing the action comprises adjusting a beam emitted by a probe towards a specular reflector. The individual blocks of the flow chart represent steps that may be performed in accordance with the method 650. Additional embodiments may perform the steps shown in a different sequence and/or additional embodiments may include additional steps not shown in FIG. 10. The technical effect of the method 650 is the steering and or focusing of an ultrasound beam emitted by the probe towards a specular reflector in a manner so that the reflected beam contacts a transducer array of the probe.

At step 652, the controller 116 controls the acquisition of ultrasound channel data. According to an embodiment, the ultrasound channel data may comprise normal ultrasound channel data or the ultrasound channel data may be acquired as part of a scout scan configured specifically to detect the position of the specular reflector. At step 654, the processor 110 identifies a subset of the ultrasound channel data with a specular reflector signature. Next, at step 656, the processor 110 implements a specular reflector processing technique to identify the position and/or the orientation of the specular reflector based on the identified subset of the ultrasound channel data. Steps 652, 654 and 656 are very similar to steps 202, 204, and 206 respectively that were previously described with respect to FIG. 2. Steps 652, 654, and 656 will therefore not be described with respect to the method 650.

Next, at step 658, the controller 116 determines if it is desired to acquire additional ultrasound channel data. If it is desired to acquire additional ultrasound channel data, the method 650 advances to step 660. If it is not desired to acquire additional ultrasound channel data, the method ends.

If additional ultrasound channel data is desired, the controller 116 adjusts the beam based on the calculated position and orientation of the specular reflector. Adjusting the beam may include adjusting multiple beam parameters, either alone or in combination.

Figure 11:
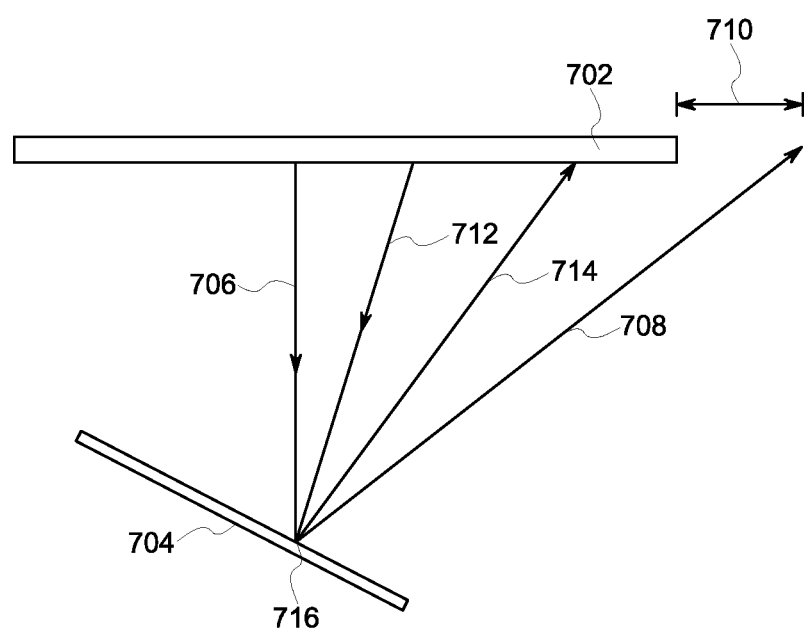
FIG. 11 is a schematic representation of an imaging configuration in accordance with an embodiment.

FIG. 11 is a schematic representation of an imaging configuration in accordance with an embodiment. The imaging configuration includes a transducer array 702 and a specular reflector 704. The imaging configuration shows a first transmit beam 706 and a first reflected beam 708. Note that the first reflected beam 708 does not contact the transducer array 710. Since the first reflected beam 708 does not contact the transducer array 710, it is not possible to use the first transmit beam 706 and the first reflected beam 710 to determine information about the specular reflector 704. However, referring back to FIG. 10, depending upon the relative geometries of the transducer array 710 and the specular reflector 704, it may be possible to adjust the beam in order to gain more information about the specular reflector 704.

For example, FIG. 11 also includes a second transmit beam 712 and a second reflected beam 714. The first transmit beam 706 and the second transmit beam 712 both contact the specular reflector at point 716. However, note how the second reflected beam 714 contacts the transducer array 702 whereas the first reflected beam did not contact the transducer array 702. FIG. 11 exhibits one exemplary way that the controller 116 may adjust the transmit beam at step 670 to ensure that the reflected beam contacts the transducer array. Additionally, when imaging a specular reflector, it is desirable for the transmit beam to be focused on the specular reflector. By using the information about the position and/or the orientation of the specular reflector obtained during step 656 of the method 650, the controller 116 may adjust the parameters of one or more subsequent beams directed adapted to image the specular reflector. After the controller 116 has made any necessary adjustments to beam, the method 650 may return to step 652. Steps 652, 654, 656, 658, and 670 may be iteratively performed as many times as desired or necessary.

Other embodiments may interleave standard imaging frames with one or more frames that are specifically steered and/or focused towards the specular reflector based on position or orientation information of the specular reflector calculated from previously acquired ultrasound channel data. For many applications, it would not be necessary or desirable to transmit beams that are specifically steered towards the specular reflector during every line. Instead it may be preferable to transmit a small percentage of the beams towards the specular reflect. According to an exemplary embodiment, it may be desirable for approximately 10% of the transmit beams to be specifically steered towards the specular reflector. The other 90% of the transmit beams may be beams adapted to acquire standard ultrasound imaging frames, such as B-mode or any other ultrasound mode. It should be appreciated by those skilled in the art that other embodiments may interleave standard frames with frames steered directly towards the specular reflector at a different ratio than that described above. The number of frames that are steered towards the specular reflector may also be adjustable. For example, it may be beneficial to have more frames steered towards the specular reflector when imaging or tracking a specular reflector that is moving quickly. On the other hand, if the specular reflector is relatively stationary, it may be more desirable to have a lower proportion of the acquired frames to frames directed at the specular reflector.

According to another embodiment, performing the action, as shown in step 208 of the method 200 may include sending the position and/or orientation information for the specular reflector to an external system. The external system may, for example, be a surgical navigation system.

Exemplary embodiments including both a processor and a controller were described in the above disclosure. It should be appreciated by those skilled in the art that any of the steps described hereinabove as being performed by one of the processor 110 and the controller 116 may be performed by the other of the processor 110 and the controller 116 according to other embodiments. Additionally, processing tasks attributed to either one of the processor 110 and the controller 116 may be distributed across any number of hardware components according to various embodiments.

The above described embodiments allow for the detection, display, and tracking of specular reflectors based only on ultrasound channel data. No external devices or tracking systems are required to quickly and accurately identify the location of specular reflectors in real-time. Additionally, the previously described embodiments allow for the display of more accurate images. By positively identifying specular reflectors, these techniques and systems allow for users to interpret images of regions with specular reflectors with a higher degree of confidence.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging with an ultrasound imaging system including a processor and a display device, the method comprising:
   acquiring ultrasound channel data with a probe;
   identifying, with the processor, a subset of the ultrasound channel data with a specular reflector signature, where the ultrasound channel data has not been beamformed during said identifying;
   implementing, with the processor, a specular reflector processing technique on the subset of the ultrasound channel data to calculate at least one of a position and an orientation of a specular reflector, where the ultrasound channel data has not been beamformed during said implementing;
   beamforming the ultrasound channel data using a summing technique to generate an ultrasound image after identifying the subset of the ultrasound channel data with the specular reflector signature;
   performing an action, with the processor, on the ultrasound channel data or on the ultrasound image to enhance a representation of the specular reflector in the ultrasound image based on at least one of the position and the orientation of the specular reflector.

2. The method of claim 1, wherein the probe comprises a 2D matrix array probe.

3. The method of claim 1, wherein said performing the action comprises co-displaying an enhanced representation of the specular reflector with the ultrasound image based on at least one of the position and the orientation of the specular reflector.

4. The method of claim 3, wherein the enhanced representation of the specular reflector comprises a line or a curve.

5. The method of claim 3, wherein the enhanced representation of the specular reflector comprises an icon representing the position and the orientation of the specular reflector.

6. The method of claim 1, wherein said implementing the specular reflector processing technique results in the generation of a specular image and, wherein the method further comprises displaying the specular image superimposed on the ultrasound image.

7. The method of claim 1, wherein said performing the action comprises transmitting at least one of the position and the orientation of the specular reflector to an external system.

8. The method of claim 7, wherein the external system comprises a surgical navigation system.

9. The method of claim 1, wherein said identifying the subset of the ultrasound channel data with the specular reflector signature comprises analyzing a variance of the ultrasound channel data.

10. The method of claim 1, wherein the specular reflector processing technique comprises calculating at least one of the position of the specular reflector and the orientation of the specular reflector by assuming the specular reflector reflects ultrasound energy with an angle of reflection equal to an angle of incidence.

11. The method of claim 1, wherein said performing the action comprises applying a post-processing technique to a region within a preset distance of the specular reflector in the ultrasound image to remove or reduce a haze artifact.

12. The method of claim 1, wherein said acquiring the ultrasound channel data comprises transmitting unfocused ultrasound energy.

13. An ultrasound imaging system comprising:
   a probe;
   a display device;
   a receiver in electronic communication with the probe; and
   a processor in electronic communication with the receiver and the display device, wherein the processor is programmed to:
   receive ultrasound channel data from the receiver;
   identify a subset of the ultrasound channel data with a specular reflector signature, where the ultrasound channel data has not been beamformed;
   implement a specular reflector processing technique on the subset of the ultrasound channel data to calculate at least one of a position and an orientation of a specular reflector, where the ultrasound channel data has not been beamformed; and
   beamform the ultrasound channel data to generate an ultrasound image after implementing the specular processing technique on the subset of the ultrasound channel data;
   perform an action on the ultrasound channel data or on the ultrasound image generated from the ultrasound channel data to enhance a representation of the specular reflector in the ultrasound image based on at least one of the position and the orientation of the specular reflector.

14. The ultrasound imaging system of claim 13, wherein the processor is programmed to perform the action of transmitting at least one of the position and the orientation of the specular reflector to an external system.

15. The ultrasound imaging system of claim 13, wherein the processor is programmed to perform the action of generating an enhanced image by superimposing an enhanced representation of the specular reflector on the ultrasound image and displaying the enhanced image.

16. The ultrasound imaging system of claim 15, wherein the processor is programmed to update the enhanced image in real-time.

17. The ultrasound imaging system of claim 13, wherein the processor is programmed to identify the subset of the ultrasound channel data by analyzing the ultrasound channel data to identify a subset of the ultrasound channel data with a signal distribution indicative of a specular reflector.

18. The ultrasound imaging system of claim 13, wherein the processor is programmed to control the probe to direct a beam transmitted by the probe to the specular reflector based on at least one of the position and the orientation of the specular reflector so that a reflected beam is detectable by the probe.

19. The ultrasound imaging system of claim 13, further comprising a controller in electronic communication with the probe, the processor, and the display device, wherein the controller is programmed to control the probe to acquire the ultrasound channel data and to control the processor to identify the subset of the ultrasound channel data, implement the specular reflector processing technique, and perform the action based on the at least one of the position and orientation of the specular reflector.

20. The ultrasound imaging system of claim 13, wherein the processor comprises a software beamformer or a component of a software beamformer.

* * * * *